(12) United States Patent
Desbordes et al.

(10) Patent No.: US 7,803,821 B2
(45) Date of Patent: Sep. 28, 2010

(54) FUNGICIDE N-CYCLOALKYL-CARBOXAMIDE, THIOCARBOXAMIDE AND N-SUBSTITUTED-CARBOXIMIDAMIDE DERIVATIVES

(75) Inventors: Philippe Desbordes, Lyons (FR); Ralf Dunkel, Leichlingen-Krähwinkel (DE); Stéphanie Gary, Champagne au Mont d'Or (FR); Marie-Claire Grosjean-Cournoyer, Curis-Au-Mont-d'Or (FR); Benoît Hartmann, Sainte-Foy-les-Lyon (FR); Philippe Rinolfi, Chatillon d'Azergues (FR); Arounarith Tuch, Lyons (FR); Jean-Pierre Vors, Sainte-Foy-les-Lyon (FR)

(73) Assignee: Bayer Cropscience SA (FR)

( * ) Notice: Subject to any disclaimer, the term of this patent is extended or adjusted under 35 U.S.C. 154(b) by 0 days.

(21) Appl. No.: 12/311,376

(22) PCT Filed: Sep. 28, 2007

(86) PCT No.: PCT/EP2007/060299
§ 371 (c)(1), (2), (4) Date: Mar. 27, 2009

(87) PCT Pub. No.: WO2008/037789
PCT Pub. Date: Apr. 3, 2008

(65) Prior Publication Data
US 2009/0270461 A1   Oct. 29, 2009

(30) Foreign Application Priority Data
Sep. 29, 2006   (EP) .................................. 06356119

(51) Int. Cl.
*A61K 31/44* (2006.01)
*A61K 31/497* (2006.01)
*A01N 43/48* (2006.01)
*C07D 401/00* (2006.01)

(52) U.S. Cl. .................. 514/341; 504/253; 504/239; 546/275.4; 514/252.13; 514/252.14; 544/333

(58) Field of Classification Search ............ 546/283.4, 546/275.4; 514/277, 341, 252.13, 252.14; 504/253, 239; 544/333
See application file for complete search history.

(56) References Cited

FOREIGN PATENT DOCUMENTS

| EP | 0 891 975 | 1/1999 |
|---|---|---|
| EP | 0891975 | 1/1999 |
| WO | WO 01/11966 | 2/2001 |
| WO | WO 2004/074280 | 9/2004 |
| WO | WO 2006/120224 | 11/2006 |
| WO | WO2006120224 | * 11/2006 |

OTHER PUBLICATIONS

Patani et. al., "Bioisosterism: A Rational Approach in Drug Design", Chem. Rev. 1996, 96, pp. 3147-3176.*

* cited by examiner

*Primary Examiner*—Janet L. Andres
*Assistant Examiner*—Binta Robinson
(74) *Attorney, Agent, or Firm*—Ostrolenk Faber LLP

(57) ABSTRACT

The present invention relates to N-cycloalkyl-carboxamide, N-cycloalkyl-thiocarboxamide and N-cycloalkyl-N-substituted carboximidamide derivatives of formula (I) wherein A represents carbo-linked, 5-membered heterocyclyl groups, T represents O, S, $NR^c$, $N-OR^d$, $N-NR^cR^d$ or $N-CN$, $Z^1$ represents cycloalkyl groups and $Z^2$ and $Z^3$, $W^1$ to $W^5$ represent various substituents; their process of preparation, their use as fungicide active agents, particularly in the form of fungicide compositions, and methods for the control of phytopathogenic fungi, notably of plants, using these compounds or compositions.

17 Claims, No Drawings

FUNGICIDE N-CYCLOALKYL-CARBOXAMIDE, THIOCARBOXAMIDE AND N-SUBSTITUTED-CARBOXIMIDAMIDE DERIVATIVES

CROSS REFERENCE TO RELATED APPLICATIONS(S)

The present application is a 35 U.S.C §371 national phase conversion of International Application No. PCT/EP2007/060299 filed Sep. 28, 2007, which claims priority of European Application No. 06356119.5 filed Sep. 29, 2006.

The present invention relates to N-cycloalkyl-carboxamide, N-cycloalkyl-thiocarboxamide and N-cycloalkyl-N-substituted carboximidamide derivatives, their process of preparation, their use as fungicide active agents, particularly in the form of fungicide compositions, and methods for the control of phytopathogenic fungi, notably of plants, using these compounds or compositions.

International patent application WO-01/11966 generically mentions certain haloalkyl-2-pyridyl-methylene-heterocyclyl-amide derivatives. However, there is no disclosure in this document of any such derivative substituted by any cycloalkyl group.

International patent application WO-2004/074259 discloses GABAA receptor-bondable compounds of the following formula:

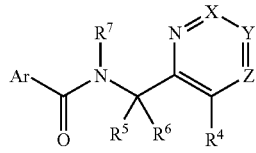

wherein Ar can represent a 5- to 10-heterocycle, $R^7$ can represent a $C_3$-$C_7$-cycloalkyl while X, Y and Z can represent N or $CR^1$, at least one representing N.

However, there is no disclosure in this document of any compound including a 5-membered heterocycle or a cycloalkyl in the nitrogen atom.

International patent application WO-2006/120224 discloses certain N-cycloalkyl-carboxamide derivatives that do not form part of the present invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides N-cycloalkyl-carboxamide derivatives of formula (I)

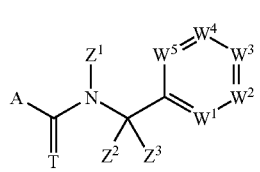

(I)

wherein
A represents a carbo-linked unsaturated or partially saturated, 5-membered heterocyclyl group that can be substituted by up to four groups $R^a$;
T represents O, S, $NR^c$, N—$OR^d$, N—$NR^cR^d$ or N—CN;
$Z^1$ represents a non substituted $C_3$-$C_7$-cycloalkyl or a $C_3$-$C_7$ cycloalkyl substituted by up to 10 atoms or groups that can be the same or different and that can be selected in the list consisting of halogen atoms; cyano; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-($C_1$-$C_8$-alkyl)aminocarbonyl;
$Z^2$ and $Z^3$ independently represent a hydrogen atom; a halogen atom; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-alkynyl; cyano; nitro; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-($C_1$-$C_8$-alkyl)amino; $C_1$-$C_8$-alkoxycarbonyl; $C_1$-$C_8$-alkylcarbonyl; $C_1$-$C_8$-alkylcarbamoyl; di-($C_1$-$C_8$-alkyl)carbamoyl; N—$C_1$-$C_8$-alkyl-$C_1$-$C_8$-alkoxycarbamoyl; or
$Z^2$ and $Z^3$ together with the carbon atom to which they are linked can form a substituted or non substituted $C_3$-$C_7$ cycloalkyl;
$W^1$ to $W^5$ independently represent N or $CR^b$, at least one of $W^1$ to $W^5$ representing N;
$R^a$ independently represents a hydrogen atom; halogen atom; cyano; nitro; amino; sulfanyl; hydroxyl; pentafluoro-λ-6-sulfanyl; $C_1$-$C_8$-alkylamino; di-($C_1$-$C_8$-alkyl)amino; tri($C_1$-$C_8$-alkyl)silyl; tri($C_1$-$C_8$-alkyl)silyl-$C_1$-$C_8$-alkyl; $C_1$-$C_8$-alkylsulfanyl; $C_1$-$C_8$-halogenoalkylsulfanyl comprising up to 9 halogen atoms that can be the same or different; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_1$-$C_8$-alkoxy; $C_1$-$C_8$-alkoxy-$C_1$-$C_8$-alkyl; $C_1$-$C_8$-halogenoalkoxy comprising up to 9 halogen atoms that can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$-alkylsulphinyl; $C_1$-$C_8$-alkylsulphonyl; $C_1$-$C_8$alkoxyimino; ($C_1$-$C_8$-alkoxyimino)-$C_1$-$C_8$-alkyl; (benzyloxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-($C_1$-$C_8$-alkyl)aminocarbonyl;
$R^b$ independently represents a hydrogen atom; halogen atom; nitro; cyano; hydroxyl sulphanyl; amino; pentafluoro-λ6-sulphanyl; $C_1$-$C_8$-alkyl; $C_1$-$C_8$-halogenoalkyl comprising up to 9 halogen atoms that can be the same or different; $C_1$-$C_8$-alkylamino; di-($C_1$-$C_8$-alkyl)amino; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_1$-$C_8$-alkylsulphanyl; $C_1$-$C_8$-halogenoalkylsulphanyl comprising up to 9 halogen atoms that can be the same or different; $C_1$-$C_8$-alkylsulphenyl, $C_1$-$C_8$-halogenoalkylsulphenyl comprising up to 9 halogen atoms that can be the same or different, $C_1$-$C_8$-alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different $C_2$-$C_8$-alkenyloxy; $C_2$-$C_8$-halogenoalkenyloxy comprising up to 9 halogen atoms that can be the same or different; $C_2$-$C_8$-alkinyloxy; $C_2$-$C_8$-halogenoalkinyloxy comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-($C_1$-$C_8$-alkyl)aminocarbonyl; $C_1$-$C_8$-alkylcarbonyloxy; $C_1$-$C_8$-halogenoalkylcarbonyloxy comprising up to 9 halogen atoms that can be the same or different; $C_1$-$C_8$-alkylcarbonylamino; $C_1$-$C_8$-alkylaminocarbonyloxy; di-($C_1$-$C_8$-alkyl)aminocarbonyloxy; $C_1$-$C_8$-alkyloxycarbonyloxy; $C_1$-$C_8$-alkoxyimino; ($C_1$-$C_8$-alkoxyimino)-$C_1$-$C_8$-alkyl; ($C_1$-$C_8$-alkenyloxyimino)-$C_1$-$C_8$-alkyl; ($C_1$-$C_8$-alkynyloxyimino)-$C_1$-$C_8$-alkyl (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl phenyl that can be substituted by up to 5 groups Q; benzyloxy that can be substituted by up to 5 groups Q; benzylsulphanyl that can be substituted by up to 5 groups Q; benzylamino that can be substituted by up to 5 groups Q; phenoxy that can be substituted by up to 5 groups Q; phenylamino that can be substituted by up to 5 groups Q; phenylsulphanyl that can be substituted by up to 5 groups Q; benzyl that can be substituted by up to 5 groups Q; pyridinyl that can be substituted by up to four groups Q and pyridinyloxy that can be substituted by up to four groups Q;

$R^c$ and $R^d$, that can be the same or different, represent a hydrogen atom; $C_1$-$C_8$-alkyl $C_1$-$C_8$-halogenoalkyl comprising up to 9 halogen atoms that can be the same or different; $C_1$-$C_8$-alkoxy-$C_1$-$C_8$-alkyl; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; phenylsulphonyl that can be substituted by up to 5 groups Q;

Q, that can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; ($C_1$-$C_8$-alkoxyimino)-$C_1$-$C_8$-alkyl;

as well as salts, N-oxides, metallic complexes, metalloidic complexes and optically active or geometric isomers thereof; provided that $R^b$ within $W^2$ to $W^5$ does not represent a $C_1$-$C_8$-halogenoalkyl when $W^1$ represents N and that $R^b$ within $W^1$ to $W^4$ does not represent a $C_1$-$C_8$-halogenoalkyl when $W^5$ represents N.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods which are known per se by the man ordinary skilled in the art.

According to the invention, the following generic terms are generally used with the following meanings:

halogen means fluorine, chlorine, bromine or iodine;

heteroatom can be nitrogen, oxygen or sulphur;

halogenated groups, notably haloalkyl, haloalkoxy and cycloalkyl groups, can comprise up to nine identical or different a halogen atoms;

any alkyl group, alkenyl group or alkynyl group can be straight or branched, the term "aryl" means phenyl or naphthyl, optionally substituted by one to five groups selected in the list consisting of halogen, [$C_1$-$C_6$]-alkyl, [$C_1$-$C_6$]-haloalkyl, [$C_2$-$C_6$]-alkenyl, [$C_2$-$C_6$]-haloalkenyl, [$C_2$-$C_6$]-alkynyl, [$C_2$-$C_6$]-haloalkynyl, [$C_1$-$C_6$]-alkoxy, [$C_1$-$C_4$]-alkoxy-[$C_1$-$C_4$]-alkyl, [$C_1$-$C_4$]-alkoxy-[$C_1$-$C_4$]-alkoxy, [$C_1$-$C_6$]-haloalkoxy and [$C_1$-$C_4$]-haloalkoxy-[$C_1$-$C_4$]-alkyl;

in the case of an amino group or the amino moiety of any other amino-containing group, substituted by two substituents that can be the same or different, the two substituents together with the nitrogen to which they are attached can form a heterocyclyl group, preferably a 5 to 7-membered heterocyclyl group, that can be substituted and can contain other hetero atoms, for example morpholino or piperidinyl.

Preferred compounds of formula (I) according to the invention are those wherein A is selected in the list consisting of:

A¹

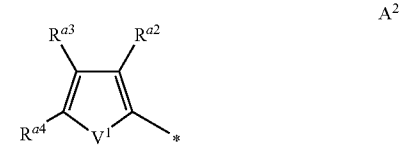

A²

-continued

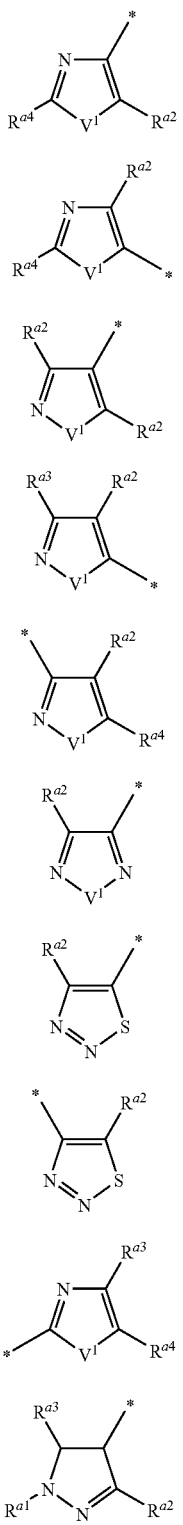

wherein:
- * represents the attachment point to the carbonyl group;
- $V^1$ represents O, S or $NR^{a1}$;
- $R^{a1}$ represents a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl;

$R^{a2}$ and $R^{a3}$, that can be the same or different, represent a hydrogen atom; a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl;

$R^{a4}$ represents a hydrogen atom, a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl; $C_1$-$C_8$-alkylsulfanyl; amino; $C_1$-$C_8$-alkylamino; di-($C_1$-$C_8$-alkyl)amino; $C_1$-$C_8$-alkyloxycarbonyl.

More preferred compounds of formula (I) according to the invention are those wherein A is selected in the list consisting of:

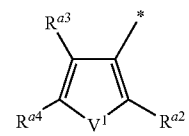

$A^1$

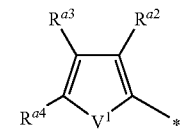

$A^2$

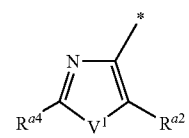

$A^3$

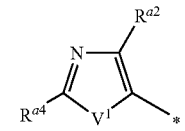

$A^4$

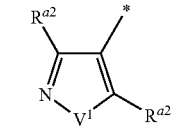

$A^5$

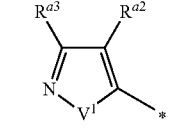

$A^6$

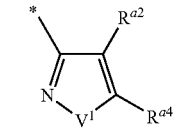

$A^7$

-continued

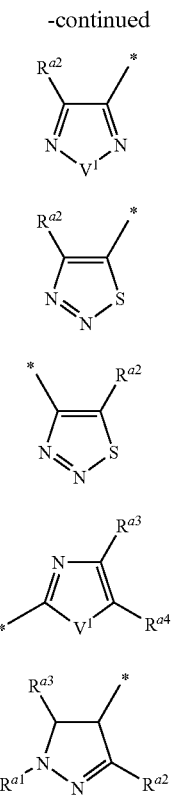

wherein:
-* represents the attachment point to the carbonyl group;
$V^1$ represents O, S or $NR^{a1}$;
$R^{a1}$ represents a hydrogen atom; $C_1$-$C_8$-alkyl; $C_1$-$C_8$-alkoxy-$C_1$-$C_8$-alkyl;
$R^{a2}$ represents $C_1$-$C_8$-alkyl; $C_1$-$C_8$-halogenoalkyl comprising up to 9 halogen atoms that can be the same or different; $C_1$-$C_8$-alkoxy;
$R^{a3}$ represents a hydrogen atom; a halogen atom; $C_1$-$C_8$-alkyl;
$R^{a4}$ represents a hydrogen atom, a halogen atom; $C_1$-$C_8$-alkyl; $C_1$-$C_8$-halogenoalkyl comprising up to 9 halogen atoms that can be the same or different.

Other more preferred compounds of formula (I) according to the invention are those wherein
A represents $A^5$;
$V^1$ represents $NR^{a1}$;
$R^{a1}$ represents $C_1$-$C_8$-alkyl;
$R^{a2}$ and $R^{a4}$, that can be the same or different represent a hydrogen atom; a halogen atom; $C_1$-$C_8$-alkyl; $C_1$-$C_8$-halogenoalkyl comprising up to 9 halogen atoms that can be the same or different.

Other more preferred compounds of formula (I) according to the invention are those wherein
A represents $A^4$;
$V^1$ represents S;
$R^{a2}$ represents a $C_1$-$C_8$-alkyl; $C_1$-$C_8$-halogenoalkyl comprising up to 9 halogen atoms that can be the same or different;
$R^{a4}$ represents a hydrogen atom; $C_1$-$C_8$-alkyl; $C_1$-$C_8$-halogenoalkyl comprising up to 9 halogen atoms that can be the same or different.

Other preferred compounds of formula (I) according to the invention are those wherein T represents an oxygen atom or a sulphur atom.

Other preferred compounds of formula (I) according to the invention are those wherein $Z^1$ represents cyclopropyl.

Other preferred compounds of formula (I) according to the invention are those wherein $Z^2$ and $Z^3$ independently represent a hydrogen atom or $C_1$-$C_8$ alkyl.

Other preferred compounds of formula (I) according to the invention are those wherein
$W^1$ represents N;
$W^2$ to $W^5$ independently represent $CR^b$;
$R^b$ independently represent a hydrogen atom; halogen atom; $C_1$-$C_8$-alkyl; $C_1$-$C_8$-alkoxy; $C_1$-$C_8$-halogenoalkoxy comprising up to 9 halogen atoms that can be the same or different; phenoxy that can be substituted by up to 5 groups Q.

Other preferred compounds of formula (I) according to the invention are those wherein
$W^2$ represents N;
$W^1$ and $W^3$ to $W^5$ independently represent $CR^b$;
$R^b$ independently represent a hydrogen atom; halogen atom; $C_1$-$C_8$-alkyl; —$C_8$-halogenoalkyl comprising up to 9 halogen atoms that can be the same or different $C_1$-$C_8$-alkoxy; $C_1$-$C_8$-halogenoalkoxy comprising up to 9 halogen atoms that can be the same or different; phenoxy that can be substituted by up to 5 groups Q.

Other preferred compounds of formula (I) according to the invention are those wherein
$W^3$ represents N;
$W^1$, $W^2$, $W^4$ and $W^5$ independently represent $CR^b$;
$R^b$ independently represent a hydrogen atom; halogen atom; $C_1$-$C_8$-alkyl; $C_1$-$C_8$-halogenoalkyl comprising up to 9 halogen atoms that can be the same or different $C_1$-$C_8$-alkoxy; $C_1$-$C_8$-halogenoalkoxy comprising up to 9 halogen atoms that can be the same or different; phenoxy that can be substituted by up to 5 groups Q.

Other preferred compounds of formula (I) according to the invention are those wherein Q represents a halogen atom; $C_1$-$C_8$-alkyl; $C_1$-$C_8$-alkoxy; $C_1$-$C_8$-halogenoalkyl comprising up to 9 halogen atoms that can be the same or different; $C_1$-$C_8$-halogenoalkoxy comprising up to 9 halogen atoms that can be the same or different.

The above mentioned preferences with regard to the substituents of the compounds of formula (I) according to the invention can be combined in various manners, either individually, partially or entirely. These combinations of preferred features thus provide sub-classes of compounds according to the invention. Examples of such sub-classes of preferred compounds according to the invention can combine:
  preferred features of A with preferred features of one or more of T, $Z^1$ to $Z^3$, $W^1$ to $W^5$, $R^a$ to $R^d$, $V^1$ and Q;
  preferred features of T with preferred features of one or more of A, $Z^1$ to $Z^3$, $W^1$ to $W^5$, $R^a$ to $R^d$, $V^1$ and Q;
  preferred features of $Z^1$ to $Z^3$ with preferred features of one or more of A, T, $W^1$ to $W^5$, $R^a$ to $R^d$, $V^1$ and Q;
  preferred features of $W^1$ to $W^5$ with preferred features of one or more of A, T, $Z^1$ to $Z^3$, $R^a$ to $R^d$, $V^1$ and Q;
  preferred features of $R^a$ to $R^d$, with preferred features of one or more of A, T, $Z^1$ to $Z^3$, $W^1$ to $W^5$, $V^1$ and Q;
  preferred features of $V^1$ with preferred features of one or more of A, T, $Z^1$ to $Z^3$, $W^1$ to $W^5$, $R^a$ to $R^d$, and Q;
  preferred features of $V^1$ with preferred features of one or more of A, T, $Z^1$ to $Z^3$, $W^1$ to $W^5$, $R^a$ to $R^d$ and $V^1$.

In these combinations of preferred features of the substituents of the compounds according to the invention, the said preferred features can also be selected among the more preferred features of each of A, T, $Z^1$ to $Z^3$, $W^1$ to $W^5$, $R^a$ to $R^d$, $V^1$ and Q; so as to form most preferred subclasses of compounds according to the invention.

The present invention also relates to a process for the preparation of compounds of formula (I).

Thus according to a further aspect of the present invention, there is provided a process P1 for the preparation of a compound of formula (I) wherein T represents O, as illustrated by the following reaction scheme:

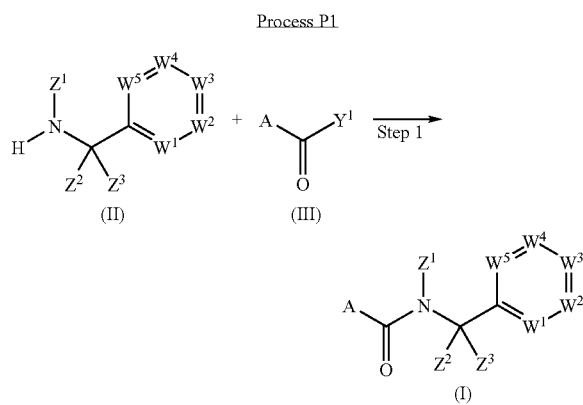

wherein
A, $Z^1$ to $Z^3$, $W^1$ to $W^5$ are as herein-defined;
$Y^1$ represents a halogen atom or a leaving group.

In process P1 according to the invention, step 1 can be performed if appropriate in the presence of a solvent and if appropriate in the presence of an acid binder.

N-cycloalkyl-amine derivatives of formula (II) are known or can be prepared by known processes such as reductive amination of aldehyde or ketone (Bioorganics and Medicinal Chemistry Letters, 2006, p 2014 synthesis of compounds 7 and 8), or reduction of imines (Tetrahedron, 2005, p 11689), or nucleophilic substitution of halogen, mesylate or tosylate (Journal of Medicinal Chemistry, 2002, p 3887 preparation of intermediate for compound 28)

Carboxylic acid derivatives of formula (III) are known or can be prepared by known processes (WO-93/11117; EP-A 0 545 099; Nucleosides & Nucleotides, 1987, p 737-759, Bioorg. Med. Chem., 2002, p 2105-2108).

Suitable acid binders for carrying out process P1 according to the invention are in each case all inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, diisopropylethylamine, tributylamine, N,N-dimethylaniline, pyridine, N methylpiperidine, N,N-dimethylaminopyridine, diazabicyclooctane (DABCO), diazabicyclononene (DBN) or diazabicycloundecene (DBU). It is also possible to work in the absence of an additional condensing agent or to employ an excess of the amine component, so that it simultaneously acts as acid binder agent.

Suitable solvents for carrying out process P1 according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out process P1 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use micro-wave technology.

Process P1 according to the invention is generally independently carried out under atmospheric pressure. However, in each case, it is also possible to operate under elevated or reduced pressure.

When carrying out step 1 of process P1 according to the invention, generally 1 mol or other an excess of the acid derivative of formula (III) and from 1 to 3 mol of acid binder are employed per mole of amine of formula (II). It is also possible to employ the reaction components in other ratios.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

According to a further aspect according to the invention, there is provided a second process P2 for the preparation of compound of formula (I), wherein T represents S, and illustrated according to the following reaction scheme:

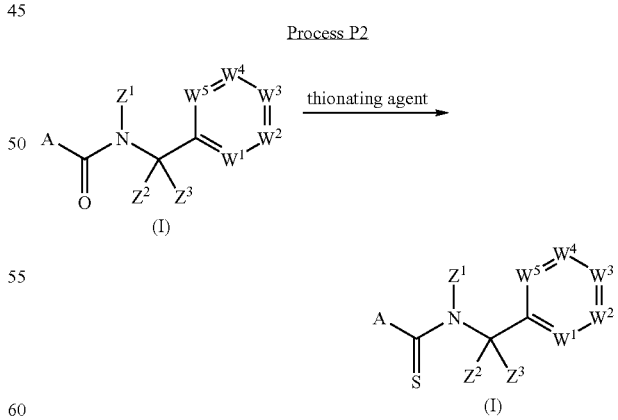

wherein A, $Z^1$ to $Z^3$, $W^1$ to $W^5$ are as herein-defined.

Process P2 can be performed in the presence of a thionating agent.

Starting amide derivatives of formula (I) can be prepared according to process P1.

Suitable thionating agents for carrying out process P2 according to the invention can be sulphur (S), sulfhydric acid (H₂S), sodium sulfide (Na₂S), sodium hydrosulfide (NaHS), boron trisulfide (B₂S₃), bis(diethylaluminium) sulfide ((AlEt₂)₂S), ammonium sulfide ((NH₄)₂S), phosphorous pentasulfide (P₂S₅), Lawesson's reagent (2,4-bis(4-methoxyphenyl)-1,2,3,4-dithiadiphosphetane 2,4-disulfide) or a polymer-supported thionating reagent such as described in *J. Chem. Soc. Perkin* 1, (2001), 358, in the presence or in the absence, of a catalytic or stoechiometric or more, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methylpiperidine.

Suitable solvents for carrying out process P2 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichlorethane; ethers, such as diethyl ether, diisopropyl ether, methyl t-butyl ether, methyl t-amyl ether, dioxane, tetrahydrofuran, 1,2-dimethoxyethane or 1,2-diethoxyethane; nitriles, such as acetonitrile, propionitrile, n- or i-butyronitrile or benzonitrile; sulphurous solvents, such as sulpholane or carbon disulfide.

When carrying out process P2 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Process P2 according to the invention is generally carried out under atmospheric pressure. It is also possible to operate under elevated or reduced pressure.

When carrying out process P2 according to the invention, 1 mole or an excess of the sulphur equivalent of the thionating agent and from 1 to 3 moles of the base can be employed per mole of the amide derivative (II).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

According to a further aspect according to the invention, there is provided a third process P3 for the preparation of compound of formula (I), wherein T represents $NR^c$, $N—OR^d$, $N—NR^cR^d$, or $N—CN$, and illustrated according to the following reaction scheme:

Process P3

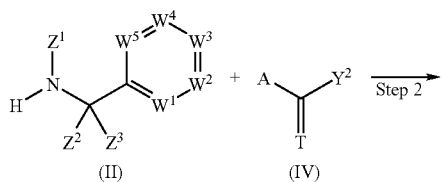

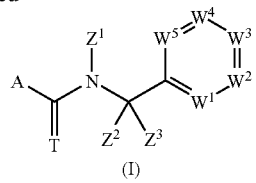

(I)

wherein

A, $Z^1$ to $Z^3$, $W^1$ to $W^5$, $R^c$ and $R^d$, are as herein-defined;

$Y^2$ represents a chlorine atom.

In process P3 according to the invention, step 2 can be performed in the presence of an acid binder and in the presence of a solvent.

N-cycloalkyl-amine derivatives of formula (II) are known or can be prepared by known processes such as reductive amination of aldehyde or ketone (Bioorganics and Medicinal Chemistry Letters, 2006, p 2014 synthesis of compounds 7 and 8), or reduction of imines (Tetrahedron, 2005, p 11689), or nucleophilic substitution of halogen, mesylate or tosylate (Journal of Medicinal Chemistry, 2002, p 3887 preparation of intermediate for compound 28).

N-substituted carboximidoyl chloride of formula (IV) are known or can be prepared by known processes, for example as described in Houben-Weyl, "Methoden der organischen Chemie" (1985), E5/1, 628-633 and Patai, "The chemistry of amidines and imidates" (1975), 296-301.

Suitable acid binders for carrying out process P3 according to the invention can be inorganic and organic bases which are customary for such reactions. Preference is given to using alkaline earth metal or alkali metal hydroxides, such as sodium hydroxide, calcium hydroxide, potassium hydroxide or other ammonium hydroxide derivatives; alkali metal carbonates, such as sodium carbonate, potassium carbonate, potassium bicarbonate, sodium bicarbonate; alkali metal or alkaline earth metal acetates, such as sodium acetate, potassium acetate, calcium acetate; alkaline earth metal or alkali metal hydrides, such as sodium hydride or potassium hydride; alkaline earth metal or alkali metal alcoolates, such as sodium methylate, sodium ethylate, sodium propylate or potassium t-butylate; and also tertiary amines, such as trimethylamine, triethylamine, tributylamine, N,N-dimethylaniline, pyridine, N-methylpiperidine, N,N-dimethyl-aminopyridine, diazabicyclooctane (DABCO), diazabicyclononene (DBN) or diazabicycloundecene (DBU); or a polymer-supported acid scavenger (for example as detailed in http://www.iris-biotech.de/downloads/scavengers.pdf).

It is also possible to work in the absence of any additional acid binder.

Suitable solvents for carrying out process P3 according to the invention can be customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichlorethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, or sulphones, such as sulpholane.

When carrying out process P3 according to the invention, the reaction temperatures can be varied within a relatively wide range. In general, these processes are carried out at temperatures from 0° C. to 160° C., preferably from 10° C. to 120° C. A way to control the temperature for the processes according to the invention is to use micro-wave technology.

Process P3 according to the invention is generally carried out under atmospheric pressure. It is also possible to operate under elevated or reduced pressure.

When carrying out process P3 according to the invention, the amine derivative of formula (III) can be employed as its salt, such as chlorhydrate or any other convenient salt.

When carrying out process P3 according to the invention, 1 mole or an excess of the amine derivative of formula (III) and from 1 to 3 moles of the acid binder can be employed per mole of the N-substituted carboximidoyl chloride of formula (IV).

It is also possible to employ the reaction components in other ratios. Work-up is carried out by known methods.

In general, the reaction mixture is concentrated under reduced pressure. The residue that remains can be freed by known methods, such as chromatography or recrystallization, from any impurities that can still be present.

Compounds according to the invention can be prepared according to the above described process. It will nevertheless be understood that, on the basis of his general knowledge and of available publications, the skilled worker will be able to adapt these processes according to the specifics of each of the compounds according to the invention that is desired to be synthesized.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the crops, and that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

B1) a compound capable to inhibit the nucleic acid synthesis like benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;

B2) a compound capable to inhibit the mitosis and cell division like benomyl, carbendazim, diethofencarb, ethaboxam, fuberidazole, pencycuron, thiabendazole, thiophanate-methyl, zoxamide;

B3) a compound capable to inhibit the respiration for example as CI-respiration inhibitor like diflumetorim;

as CII-respiration inhibitor like boscalid, carboxin, fenfuram, flutolanil, furametpyr, furmecyclox, mepronil, oxycarboxin, penthiopyrad, thifluzamide;

as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

B4) a compound capable of to act as an uncoupler like dinocap, fluazinam, meptyldinocap;

B5) a compound capable to inhibit ATP production like fentin acetate, fentin chloride, fentin hydroxide, silthiofam;

B6) a compound capable to inhibit AA and protein biosynthesis like andoprim, blasticidin-S, cyprodinil, kasugamycin, kasugamycin hydrochloride hydrate, mepanipyrim, pyrimethanil;

B7) a compound capable to inhibit the signal transduction like fenpiclonil, fludioxonil, quinoxyfen;

B8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

B9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

B10) a compound capable to inhibit cell wall synthesis like benthiavalicarb, dimethomorph, flumorph, iprovalicarb, mandipropamid, polyoxins, polyoxorim, validamycin A;

B11) a compound capable to inhibit melanine biosynthesis like carpropamid, diclocymet, fenoxanil, phthalide, pyroquilon, tricyclazole;

B12) a compound capable to induce a host defence like acibenzolar-S-methyl, probenazole, tiadinil;

B13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propineb, sulphur and sulphur preparations including calcium polysulphide, thiram, tolylfluanid, zineb, ziram;

B14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy) methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy) methyl]-2,2-dimethylpropyl-1H-imidazole-1-carboxylate, 1-methyl-N-[2-(1,1,2,2-tetrafluoroethoxy) phenyl]-3-(trifluoromethyl)-1H-pyrazole-4-carboxamide, 2,3,5,6-tetrachloro-4-(methylsulfonyl) pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3-(difluoromethyl)-1-methyl-N-[2-(1,1,2,2-tetrafluoroethoxy)phenyl]-1H-pyrazole-4-carboxamide, 3-(difluoromethyl)-N-[(9R)-9-isopropyl-1,2,3,4-tetrahydro-1,4-methanonaphthalen-5-yl]-1-methyl-1H-pyrazole-4-carboxamide, 3-(difluoromethyl)-N-[(9S)-9-isopropyl-1,2,3,4-tetrahydro-1,4-methanonaphthalen-5-yl]-1-methyl-1H-pyrazole-4-carboxamide, 3-(difluoromethyl)-N-[4'-(3,3-dimethylbut-1-yn-1-yl) biphenyl-2-yl]-1-methyl-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-chloro-7-(4-methylpiperidin-1-yl)-6-(2,4,6-trifluorophenyl)[1,2,4] triazolo[1,5-a]pyrimidine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio) methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl) methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl)ethyl]-2-fluoro-4-iodonicotinamide, N-[2-(1,3-dimethylbutyl)phenyl]-5-fluoro-1,3-dimethyl-1H-pyrazole-4-carboxamide, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-{2-[3-chloro-5-(trifluoromethyl) pyridin-2-yl]ethyl}-2-(trifluoromethyl)benzamide, natamycin, N-ethyl-N-methyl-N'-{2-methyl-5-(trifluoromethyl)-4-[3-(trimethylsilyl)propoxy] phenyl}imidoformamide, N-ethyl-N-methyl-N'-{2-methyl-5-(difluoromethyl)-4-[3-(trimethylsilyl)propoxy] phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, S-allyl-5-amino-2-isopropyl-4-(2-methylphenyl)-3-oxo-2,3-dihydro-1H-pyrazole-1-carbothioate, tecloftalam, tecnazene, triazoxide, trichlamide, valiphenal, zarilamid.

The composition according to the invention comprising a mixture of a compound of formula (I) with a bactericide compound can also be particularly advantageous. Examples of suitable bactericide mixing partners can be selected in the following list: bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

Among the plants that can be protected by the method according to the invention, mention can be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

Among the diseases of plants or crops that can be controlled by the method according to the invention, mention can be made of:

Powdery mildew diseases such as:
Blumeria diseases, caused for example by *Blumeria graminis*;
Podosphaera diseases, caused for example by *Podosphaera leucotricha*;
Sphaerotheca diseases, caused for example by *Sphaerotheca fuliginea*;
Uncinula diseases, caused for example by *Uncinula necator*;

Rust diseases such as:
Gymnosporangium diseases, caused for example by *Gymnosporangium sabinae*;
Hemileia diseases, caused for example by *Hemileia vastatrix*;
Phakopsora diseases, caused for example by *Phakopsora pachyrhizi* or *Phakopsora meibomiae*;
Puccinia diseases, caused for example by *Puccinia recondita*;
Uromyces diseases, caused for example by *Uromyces appendiculatus*;

Oomycete diseases such as:
Bremia diseases, caused for example by *Bremia lactucae*;
Peronospora diseases, caused for example by *Peronospora pisi* or *P. brassicae*;
Phytophthora diseases, caused for example by *Phytophthora infestans*;
Plasmopara diseases, caused for example by *Plasmopara viticola*;
Pseudoperonospora diseases, caused for example by *Pseudoperonospora humuli* or *Pseudoperonospora cubensis*;
Pythium diseases, caused for example by *Pythium ultimum*;

Leafspot, leaf blotch and leaf blight diseases such as:
Alternaria diseases, caused for example by *Alternaria solani*;
Cercospora diseases, caused for example by *Cercospora beticola*;
Cladiosporum diseases, caused for example by *Cladiosporum cucumerinum*;
Cochliobolus diseases, caused for example by *Cochliobolus sativus*;
Colletotrichum diseases, caused for example by *Colletotrichum lindemuthanium*;
Cycloconium diseases, caused for example by *Cycloconium oleaginum*;
Diaporthe diseases, caused for example by *Diaporthe citri*;
Elsinoe diseases, caused for example by *Elsinoe fawcettii*;
Gloeosporium diseases, caused for example by *Gloeosporium laeticolor*;
Glomerella diseases, caused for example by *Glomerella cingulata*;
Guignardia diseases, caused for example by *Guignardia bidwelli*;
Leptosphaeria diseases, caused for example by *Leptosphaeria maculans*; *Leptosphaeria nodorum*;
Magnaporthe diseases, caused for example by *Magnaporthe grisea*;
Mycosphaerella diseases, caused for example by *Mycosphaerella graminicola*; *Mycosphaerella arachidicola*; *Mycosphaerella fijiensis*;
Phaeosphaeria diseases, caused for example by *Phaeosphaeria nodorum*;
Pyrenophora diseases, caused for example by *Pyrenophora teres*;
Ramularia diseases, caused for example by *Ramularia collo-cygni*;
Rhynchosporium diseases, caused for example by *Rhynchosporium secalis*;
Septoria diseases, caused for example by *Septoria apii* or *Septoria lycopercisi*;
Typhula diseases, caused for example by *Typhula incarnata*;
Venturia diseases, caused for example by *Venturia inaequalis*;

Root and stem diseases such as:
Corticium diseases, caused for example by *Corticium graminearum;*
Fusarium diseases, caused for example by *Fusarium oxysporum;*
Gaeumannomyces diseases, caused for example by *Gaeumannomyces graminis;*
Rhizoctonia diseases, caused for example by *Rhizoctonia solani;*
Tapesia diseases, caused for example by *Tapesia acuformis;*
Thielaviopsis diseases, caused for example by *Thielaviopsis basicola;*
Ear and panicle diseases such as:
Alternaria diseases, caused for example by *Alternaria* spp.
Aspergillus diseases, caused for example by *Aspergillus flavus;*
Cladosporium diseases, caused for example by *Cladosporium* spp.
Claviceps diseases, caused for example by *Claviceps purpurea;*
Fusarium diseases, caused for example by *Fusarium culmorum;*
Gibberella diseases, caused for example by *Gibberella zeae;*
Monographella diseases, caused for example by *Monographella nivalis;*
Smut and bunt diseases such as:
Sphacelotheca diseases, caused for example by *Sphacelotheca reiliana;*
Tilletia diseases, caused for example by *Tilletia caries;*
Urocystis diseases, caused for example by *Urocystis occulta;*
Ustilago diseases, caused for example by *Ustilago nuda;*
Fruit rot and mould diseases such as:
Aspergillus diseases, caused for example by *Aspergillus flavus;*
Botrytis diseases, caused for example by *Botrytis cinerea;*
Penicillium diseases, caused for example by *Penicillium expansum;*
Sclerotinia diseases, caused for example by *Sclerotinia sclerotiorum;*
Verticilium diseases, caused for example by *Verticilium alboatrum;*
Seed and soilborne decay, mould, wilt, rot and damping-off diseases such as:
Fusarium diseases, caused for example by *Fusarium culmorum;*
Phytophthora diseases, caused for example by *Phytophthora cactorum;*
Pythium diseases, caused for example by *Pythium ultimum;*
Rhizoctonia diseases, caused for example by *Rhizoctonia solani;*
Sclerotium diseases, caused for example by *Sclerotium rolfsii;*
Microdochium diseases, caused for example by *Microdochium nivale;*
Canker, broom and dieback diseases such as:
Nectria diseases, caused for example by *Nectria galligena;*
Blight diseases such as:
Monilinia diseases, caused for example by *Monilinia laxa;*
Leaf blister or leaf curl diseases such as:
Taphrina diseases, caused for example by *Taphrina deformans;*
Decline diseases of wooden plants such as:
Esca diseases, caused for example by *Phaemoniella clamydospora;*
Eutypa dyeback, caused for example by *Eutypa lata;*
Dutch elm disease, caused for example by *Ceratocystsc ulmi;*
Diseases of flowers and Seeds such as:
Botrytis diseases, caused for example by *Botrytis cinerea;*
Diseases of tubers such as:
Rhizoctonia diseases, caused for example by *Rhizoctonia solani;*
Helminthosporium diseases, caused for example by *Helminthosporium solani.*

The fungicide composition according to the invention can also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The fungicide composition according to the invention can also be used in the treatment of genetically modified organisms with the compounds according to the invention or the agrochemical compositions according to the invention. Genetically modified plants are plants into genome of that a heterologous gene encoding a protein of interest has been stably integrated. The expression "heterologous gene encoding a protein of interest" essentially means genes that give the transformed plant new agronomic properties, or genes for improving the agronomic quality of the modified plant.

The compounds or mixtures according to the invention can also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following table of compound examples and the following preparation or efficacy examples.

The following table illustrates in a non limiting manner examples of compounds according to the invention.

In the following table, M+H (or M−H) means the molecular ion peak, plus or minus 1 a.m.u. (atomic mass unit) respectively, as observed in mass spectroscopy.

In the following table, the log P values were determined in accordance with EEC Directive 79/831 Annex V.A8 by HPLC (High Performance Liquid Chromatography) on a reversed-phase column (C18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones).

The lambda max values were determined in the maxima of the chromatographic signals using the UV spectra from 190 nm to 400 nm.

TABLE

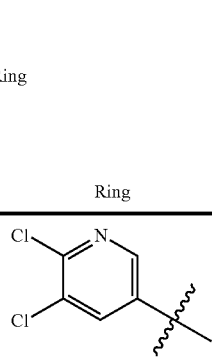

| Example | A | $V^1$ | $R^{a2}$ | $R^{a3}$ | $R^{a4}$ | T | $Z^2$ | $Z^3$ | Ring | logP | M+H |
|---|---|---|---|---|---|---|---|---|---|---|---|
| 1 | A5 | N—Me | CF3 | — | H | O | Me | H | 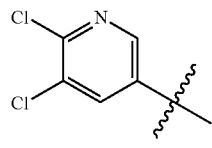 | 3.14 | 407 |
| 2 | A1 | N—Me | H | CF3 | H | O | Me | H | 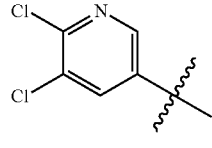 | 3.34 | 406 |
| 3 | A1 | O | Me | H | Me | O | Me | H | 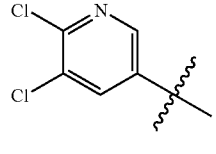 | 3.7 | |
| 4 | A5 | N—Me | Me | — | F | O | Me | H | 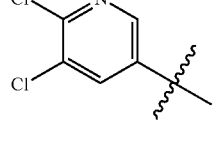 | 2.56 | 371 |
| 5 | A5 | N—Me | CHF2 | — | H | O | Me | H | 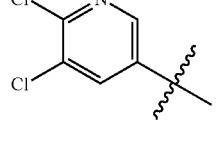 | 2.67 | 389 |
| 6 | A5 | N—Me | OMe | — | H | O | Me | H | 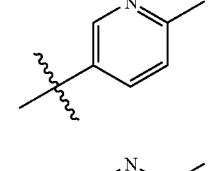 | 2.29 | 369 |
| 7 | A5 | N—Me | Me | — | F | O | H | H | 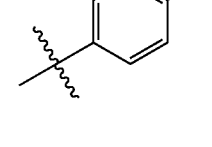 | 0.43 | |
| 8 | A5 | N—Me | CHF2 | — | H | O | H | H | 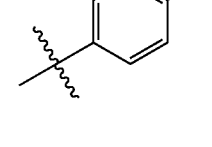 | 0.52 | 321 |

TABLE-continued
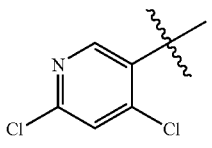
| Example | A | V$^1$ | R$^{a2}$ | R$^{a3}$ | R$^{a4}$ | T | Z$^2$ | Z$^3$ | Ring | logP | M + H |
|---|---|---|---|---|---|---|---|---|---|---|---|
| 9 | A5 | N—Me | Me | — | F | O | H | H | 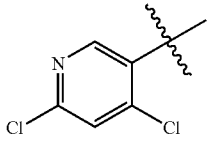 | 2.28 | 357 |
| 10 | A5 | N—Me | CHF2 | — | H | O | H | H | 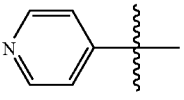 | 2.46 | 375 |
| 11 | A5 | N—Me | CF3 | — | H | O | H | H | 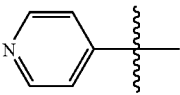 | 0.59 | 325 |
| 12 | A1 | S | I | H | H | O | H | H | 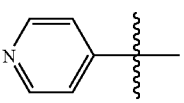 | 1.1 | 385 |
| 13 | A4 | S | CF3 | — | Me | O | H | H | 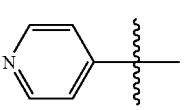 | 0.93 | 342 |
| 14 | A4 | S | CHF2 | — | Me | O | H | H | 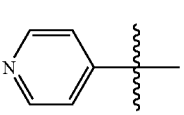 | 0.58 | 324 |
| 15 | A8 | N—Me | CF3 | — | — | O | H | H | 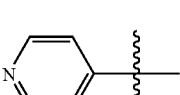 | 1.03 | 326 |
| 16 | A1 | N—Me | H | CF3 | H | O | H | H | 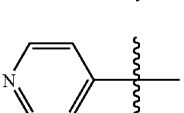 | 0.99 | 324 |
| 17 | A5 | N—Me | Me | — | F | O | Et | H | 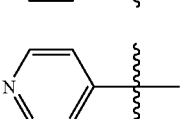 | 0.92 | 317 |
| 18 | A5 | N—Me | CHF2 | — | H | O | Et | H | 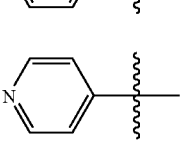 | 1.79 | |
| 19 | A5 | N—Me | OMe | — | H | O | H | H |  | | 287 |

TABLE-continued
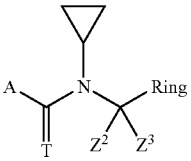
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 20 | A4 | S | CHF2 | — | Me | O | Me | H | 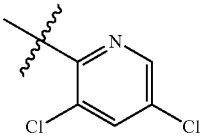 | 3.64 | 406 |
| 21 | A5 | N—Me | CF3 | — | H | O | H | H | 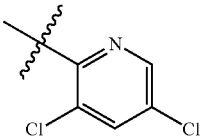 | 3.21 | 393 |
| 22 | A5 | N—Me | OEt | — | H | O | H | H | 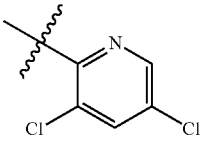 | 2.54 | 369 |
| 23 | A4 | S | CF3 | — | Me | O | H | H | 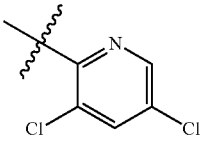 | 3.76 | 410 |
| 24 | A4 | S | CHF2 | — | Me | O | H | H | 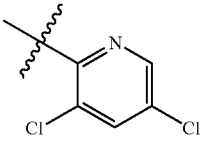 | 3.42 | 392 |
| 25 | A1 | O | Me | H | H | O | H | H | 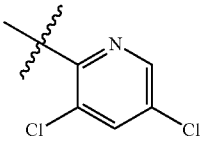 | 3.22 | 325 |
| 26 | A2 | S | I | H | H | O | H | H | 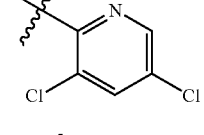 | 4.16 | 453 |
| 27 | A5 | N—Me | Me | — | H | O | Me | H | 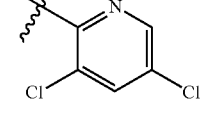 | 2.4 | 353 |
| 28 | A5 | N—Me | Me | — | F | O | Me | H | | 2.77 | 371 |

TABLE-continued
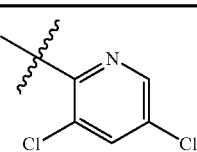
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 29 | A5 | N—Me | Me | — | F | O | H | H | 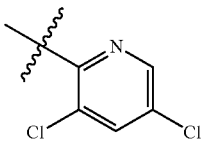 | 2.56 | 357 |
| 30 | A5 | N—Me | Me | — | F | S | Me | H | 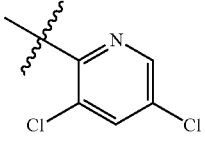 | 3.9 | 387 |
| 31 | A5 | N—Me | CHF2 | — | H | O | Me | H | 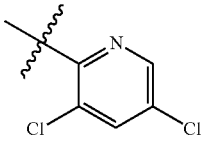 | 3.01 | 389 |
| 32 | A5 | N—Me | CHF2 | — | H | S | Me | H | 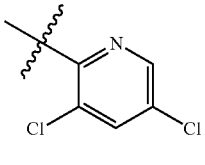 | 4.01 | 405 |
| 33 | A5 | N—Me | Et | — | F | O | Me | H | 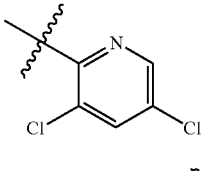 | 3.23 | 385 |
| 34 | A5 | N—Me | OMe | — | H | O | H | H | 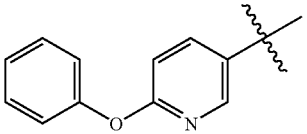 | 2.21 | 355 |
| 35 | A5 | N—Me | Me | — | F | O | H | H | 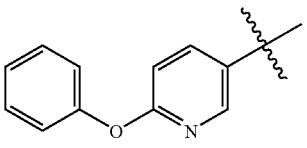 | 2.39 | 381 |
| 36 | A5 | N—Me | CHF2 | — | H | O | H | H | 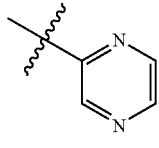 | 2.61 | 399 |
| 37 | A1 | S | I | H | H | O | Me | H |  | 2.38 | 400 |

TABLE-continued
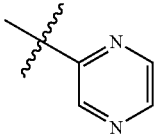
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 38 | A2 | O | H | H | H | O | Me | H | 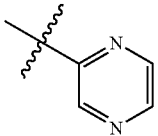 | 1.62 | 258 |
| 39 | A3 | O | Me | — | Me | O | Me | H | 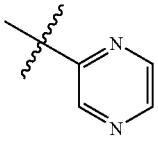 | 1.55 | 287 |
| 40 | A5 | N—Me | Me | — | H | O | Me | H | 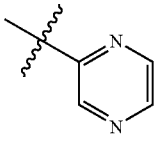 | 1.25 | 286 |
| 41 | A2 | O | Me | H | H | O | Me | H | 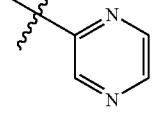 | 2.04 | 272 |
| 42 | A5 | N—Me | CHF2 | — | H | O | Me | H | 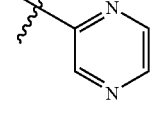 | 1.47 | 322 |
| 43 | A5 | N—Me | CHF2 | — | H | S | Me | H | 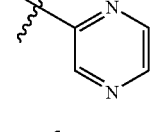 | 2.05 | 338 |
| 44 | A4 | O | Me | — | H | O | Me | H | 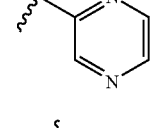 | 1.37 | 273 |
| 45 | A7 | O | H | — | Me | O | Me | H | 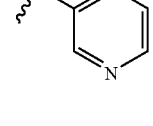 | 1.65 | 273 |
| 46 | A7 | N—Me | H | — | Me | O | Me | H |  | 1.45 | 286 |

TABLE-continued
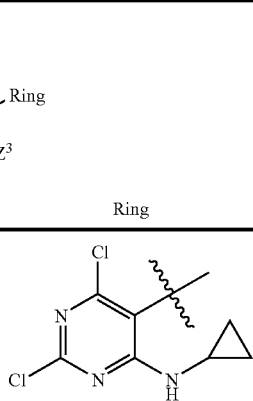
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 47 | A5 | N—Me | Me | — | F | O | H | H | 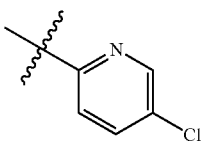 | 2.28 | 413 |
| 48 | A5 | N—Me | CF3 | — | H | O | H | H | 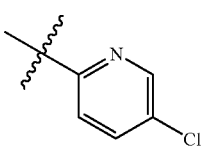 | 2.39 | |
| 49 | A5 | N—Me | OEt | — | H | O | H | H | 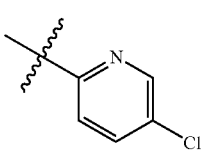 | 1.98 | |
| 50 | A1 | O | CF3 | H | Me | O | H | H | 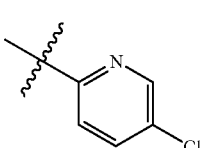 | 3.36 | |
| 51 | A4 | S | CF3 | — | Me | O | H | H | 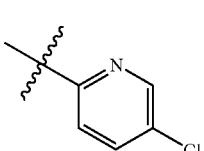 | 2.93 | |
| 52 | A4 | S | CHF2 | — | Me | O | H | H | 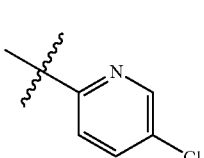 | 2.54 | |
| 53 | A2 | S | I | H | H | O | H | H | 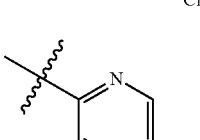 | 3.17 | |
| 54 | A5 | N—Me | CHF2 | — | H | O | H | H | | 2.08 | |
| 55 | A1 | S | I | H | H | O | H | H | 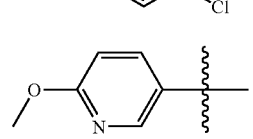 | 2.75 | 415 |

TABLE-continued
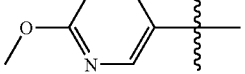
| Example | A | V$^1$ | R$^{a2}$ | R$^{a3}$ | R$^{a4}$ | T | Z$^2$ | Z$^3$ | Ring | logP | M + H |
|---|---|---|---|---|---|---|---|---|---|---|---|
| 56 | A2 | O | H | H | H | O | H | H | 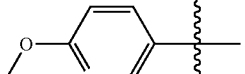 | 1.97 | 273 |
| 57 | A3 | O | Me | — | Me | O | H | H | 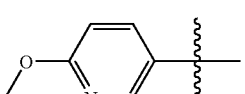 | 1.89 | 302 |
| 58 | A5 | N—Me | Me | — | H | O | H | H | 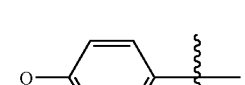 | 1.53 | 301 |
| 59 | A2 | O | Me | H | H | O | H | H | 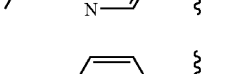 | 2.46 | 287 |
| 60 | A5 | N—Me | Me | — | F | O | H | H | 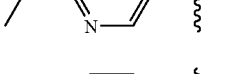 | 1.64 | 319 |
| 61 | A5 | N—Me | CHF2 | — | H | O | H | H | 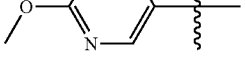 | 1.8 | 337 |
| 62 | A4 | O | Me | — | H | O | H | H | 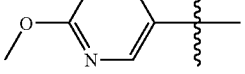 | 1.72 | 288 |
| 63 | A7 | O | H | — | Me | O | H | H | 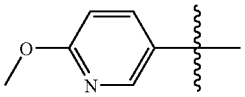 | 2.08 | 288 |
| 64 | A7 | N—Me | H | — | Me | O | H | H | 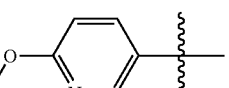 | 1.74 | 301 |
| 65 | A5 | N—Me | CF3 | — | H | O | H | H | 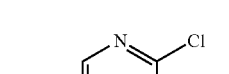 | 2.02 | 359 |
| 66 | A1 | S | I | H | H | O | H | H |  | 2.67 | 419 |

TABLE-continued
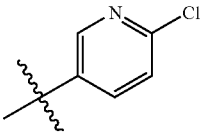
| Example | A | V$^1$ | R$^{a2}$ | R$^{a3}$ | R$^{a4}$ | T | Z$^2$ | Z$^3$ | Ring | logP | M + H |
|---|---|---|---|---|---|---|---|---|---|---|---|
| 67 | A4 | S | CF3 | — | Me | O | H | H | 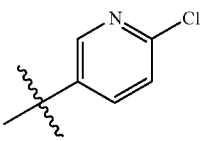 | 2.57 | 376 |
| 68 | A4 | S | CHF2 | — | Me | O | H | H | 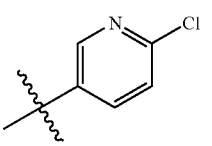 | 2.18 | 358 |
| 69 | A8 | N—Me | CF3 | — | — | O | H | H | 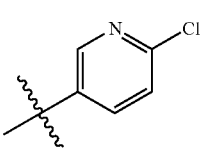 | 2.62 | 360 |
| 70 | A1 | N—Me | H | CF3 | H | O | H | H | 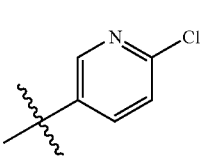 | 2.45 | 358 |
| 71 | A5 | N—Me | Me | — | F | O | H | H | 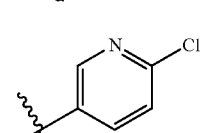 | 1.85 | 323 |
| 72 | A5 | N—Me | CHF2 | — | H | O | H | H | 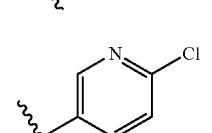 | 1.97 | 341 |
| 73 | A5 | N—Me | CHF2 | — | H | S | H | H | 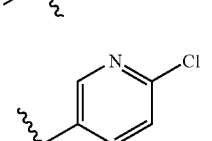 | 2.58 | 357 |
| 74 | A5 | N—Me | OMe | — | H | O | H | H | 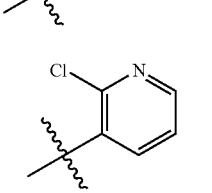 | 1.56 | 321 |
| 75 | A1 | S | I | H | H | O | Me | H |  | 2.9 | 433 |

TABLE-continued
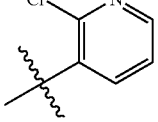
| Example | A | V¹ | R^{a2} | R^{a3} | R^{a4} | T | Z² | Z³ | Ring | logP | M + H |
|---|---|---|---|---|---|---|---|---|---|---|---|
| 76 | A2 | O | H | H | H | O | Me | H | 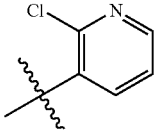 | 2.06 | 291 |
| 77 | A3 | O | Me | — | Me | O | Me | H | 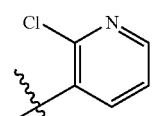 | 1.94 | 320 |
| 78 | A5 | N—Me | Me | — | H | O | Me | H | 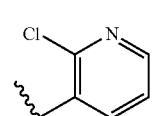 | 1.58 | 319 |
| 79 | A2 | O | Me | H | H | O | Me | H | 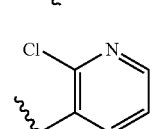 | 2.52 | 305 |
| 80 | A5 | N—Me | Me | — | F | O | Me | H | 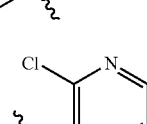 | 1.69 | 337 |
| 81 | A5 | N—Me | CHF2 | — | H | O | Me | H | 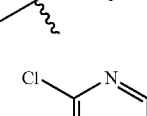 | 1.88 | 355 |
| 82 | A4 | O | Me | — | H | O | Me | H | 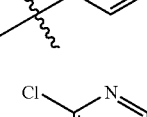 | 1.76 | 306 |
| 83 | A7 | O | H | — | Me | O | Me | H | 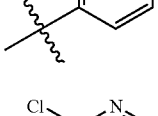 | 2.07 | 306 |
| 84 | A7 | N—Me | H | — | Me | O | Me | H |  | 1.78 | 319 |

TABLE-continued
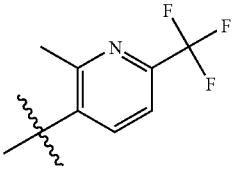
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 85 | A5 | N—Me | CF3 | — | H | O | H | H | 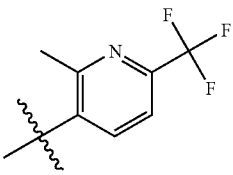 | 2.82 | 407 |
| 86 | A5 | N—Me | Me | — | F | O | H | H | 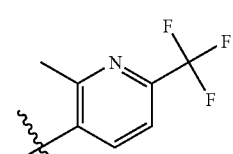 | 2.32 | 371 |
| 87 | A5 | N—Me | CHF2 | — | H | O | H | H |  | 2.51 | 389 |
| 88 | A5 | N—Me | OMe | — | H | O | H | H | 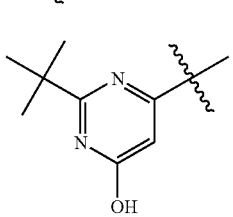 | 2.02 | 369 |
| 89 | A1 | S | I | H | H | O | H | H | 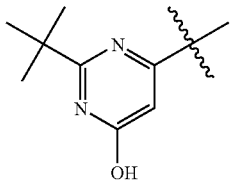 | 2.16 | 458 |
| 90 | A4 | S | CF3 | — | Me | O | H | H | 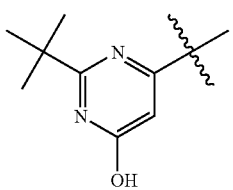 | 2.23 | 415 |
| 91 | A4 | S | CHF2 | — | Me | O | H | H | | 1.94 | 397 |

TABLE-continued
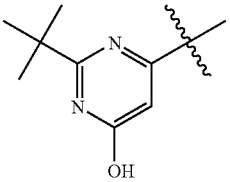
| Example | A | V$^1$ | R$^{a2}$ | R$^{a3}$ | R$^{a4}$ | T | Z$^2$ | Z$^3$ | Ring | logP | M + H |
|---|---|---|---|---|---|---|---|---|---|---|---|
| 92 | A8 | N—Me | CF3 | — | — | O | H | H | 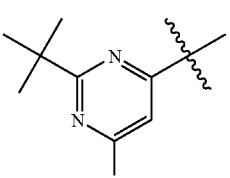 | 2.3 | 399 |
| 93 | A1 | N—Me | H | CF3 | H | O | H | H | 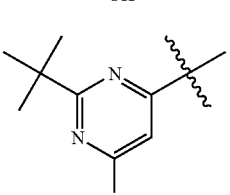 | 2.17 | 397 |
| 94 | A5 | N—Me | Me | — | F | O | H | H | 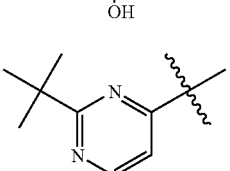 | 1.7 | 362 |
| 95 | A5 | N—Me | CHF2 | — | H | O | H | H | 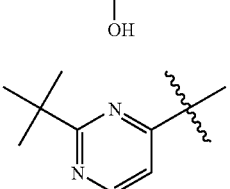 | 1.8 | 380 |
| 96 | A5 | N—Me | OMe | — | H | O | H | H | 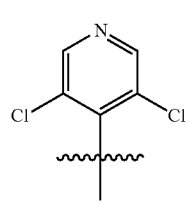 | 1.32 | 360 |
| 97 | A1 | S | I | H | H | O | H | H | 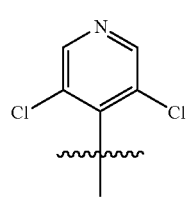 | 3.21 | 453 |
| 98 | A2 | O | H | H | H | O | H | H | 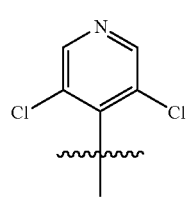 | 2.33 | 311 |

TABLE-continued
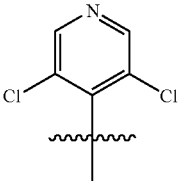
| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 99 | A3 | O | Me | — | Me | O | H | H | 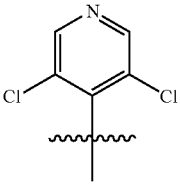 | 2.18 | 340 |
| 100 | A5 | N—Me | Me | — | H | O | H | H | 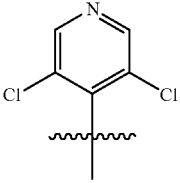 | 1.8 | 339 |
| 101 | A2 | O | Me | H | H | O | H | H | 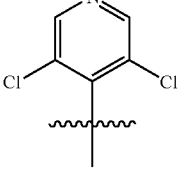 | 2.87 | 325 |
| 102 | A5 | N—Me | Me | — | F | O | H | H | 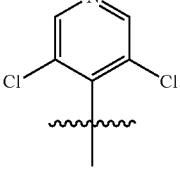 | 2.01 | 357 |
| 103 | A5 | N—Me | CHF2 | — | H | O | H | H | 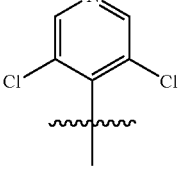 | 1.88 | 375 |
| 104 | A5 | N—Me | CHF2 | — | H | S | H | H | 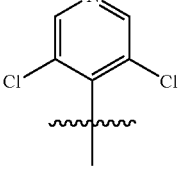 | 2.93 | 391 |
| 105 | A4 | O | Me | — | H | O | H | H | 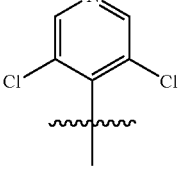 | 2.04 | 326 |

TABLE-continued

| Example | A | V¹ | R$^{a2}$ | R$^{a3}$ | R$^{a4}$ | T | Z² | Z³ | Ring | logP | M + H |
|---|---|---|---|---|---|---|---|---|---|---|---|
| 106 | A7 | O | H | — | Me | O | H | H | 3,5-dichloropyridin-4-yl | 2.4 | 326 |
| 107 | A7 | N—Me | H | — | Me | O | H | H | 3,5-dichloropyridin-4-yl | 2 | 339 |
| 108 | A5 | N—Me | CF3 | — | H | O | H | H | 3,4-dimethoxypyridin-2-yl | 1.18 | 385 |
| 109 | A1 | S | I | H | H | O | H | H | 3,4-dimethoxypyridin-2-yl | 1.47 | 445 |
| 110 | A4 | S | CHF2 | — | Me | O | H | H | 3,4-dimethoxypyridin-2-yl | 1.2 | 384 |
| 111 | A8 | N—Me | CF3 | — | — | O | H | H | 3,4-dimethoxypyridin-2-yl | 1.44 | 386 |

TABLE-continued

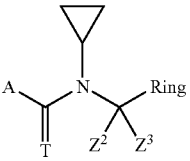

| Example | A | V¹ | R^{a2} | R^{a3} | R^{a4} | T | Z² | Z³ | Ring | logP | M + H |
|---|---|---|---|---|---|---|---|---|---|---|---|
| 112 | A1 | N—Me | H | CF3 | H | O | H | H | 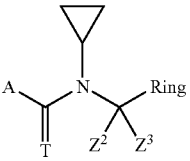 | 1.32 | 384 |
| 113 | A5 | N—Me | Me | — | F | O | H | H | 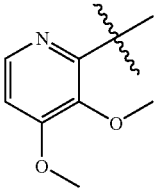 | 1.65 | 349 |
| 114 | A5 | N—Me | CHF2 | — | H | O | H | H | 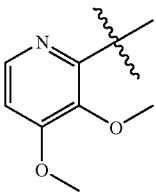 | 1.05 | 367 |
| 115 | A5 | N—Me | OMe | — | H | O | H | H | 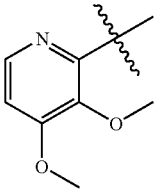 | 0.56 | 347 |

The following examples illustrate in a non-limiting manner the preparation and efficacy of the compounds of formula (I) according to the invention.

PREPARATION EXAMPLE 1

N-cyclopropyl-N-[(3,4-dimethoxypyridin-2-yl)methyl]-5-fluoro-1,3-dimethyl-1H-pyrazole-4-carboxamide (compound 113)

Step 1: preparation of N-[(3,4-dimethoxypyridin-2-yl)methyl]cyclopropylamine 1.05 ml (14.9 mmol) of cyclopropylamine was added to a solution of 695 mg (2.66 mmol) of 2-chloromethyl-3,4-dimethoxypyridinium hydrochloride in 4 ml ethanol and 4 ml of saturated aqueous sodium hydrogen carbonate. The reaction mixture was stirred for 1.5 hrs at 58° C. and extracted with ethyl acetate (3×10 ml). The combined organic layers were dried over magnesium sulphate and concentrated in vacuum. Column chromatography (gradient dichloromethane/methanol) yielded 263 mg (42% yield) of N-[(3,4-dimethoxypyridin-2-yl)methyl]cyclopropylamine.

Step 2: preparation of N-cyclopropyl-N-[(3,4-dimethoxypyridin-2-yl)methyl]-5-fluoro-1,3-dimethyl-1H-pyrazole-4-carboxamide At ambient temperature a solution of 0.14 g (0.8 mmol) of 5-fluoro-1,3-dimethyl-1H-pyrazole-4-carbonyl chloride in 2 ml of dichloromethane was added drop wise to a solution of 0.15 g (0.7 mmol) of N-[(3,4-dimethoxypyridin-2-yl)methyl]cyclopropylamine and 0.3 ml of triethylamine in 4 ml of dichloromethane. The reaction mixture was stirred for 16 hrs at ambient temperature and quenched with water. The watery layer was extracted three times with dichloromethane (3×10 ml), the combined organic layers were dried over magnesium sulphate and concentrated in vacuum. Column chromatography (gradient n-pentane/ethyl acetate) yielded 0.23 mg (92% yield) of N-cyclopropyl-N-[(3,4-dimethoxypyridin-2-yl)methyl]-5-fluoro-1,3-dimethyl-1H-pyrazole-4-carboxamide (M+H=349).

PREPARATION EXAMPLE 2

N-cyclopropyl-N-[1-pyridin-4-yl-propyl]-5-fluoro-1,3-dimethyl-1H-pyrazole-4-carboxamide (compound 17)

Step 1: preparation of N-cyclopropyl-1-pyridin-4-yl-propylamine

To a mixture of 8 g of molecular sieves and 8.4 g (148 mmol) of cyclopropylamine in 100 ml of methanol at 0° C., were successively added 11 ml of acetic acid and 10 g (74 mmol) of 4-propionyl-pyridine. The reaction mixture was stirred for 3 hrs at reflux and cooled to room temperature. A solution of 6.9 g (185 mmol) of sodium cyanoborohydride in 20 ml of methanol was added dropwise. The reaction mixture was stirred for 3 hrs at reflux, and cooled to room temperature. The reaction mixture was concentrated in vacuum to half its volume and diluted with 80 ml of dichloromethane. Heptane was added so that a solid precipitated. The solid was filtrated. The filtrate was concentrated in vacuum to give 8.7 g (66%) of N-cyclopropyl-1-pyridin-4-yl-propylamine.

Step 2: preparation of N-cyclopropyl-N-[1-pyridin-4-yl-propyl]-5-fluoro-1,3-dimethyl-1H-pyrazole-4-carboxamide At ambient temperature a solution of 0.16 g (0.93 mmol) of 5-fluoro-1,3-dimethyl-1H-pyrazole-4-carbonyl chloride in 2 ml of dichloromethane was added dropwise to a solution of 0.15 g (0.85 mmol) of N-cyclopropyl-1-pyridin-4-yl-propylamine and 0.14 ml of triethylamine in 5 ml of dichloromethane. The reaction mixture was stirred for 12 hrs at ambient temperature and then at 40° C. for 8 hrs and washed with water. The organic layers were filtrated over basic alumina and dried. Column chromatography (gradient dichloromethane/Methanol) yielded 0.18 mg (44% yield) of N-cyclopropyl-N-[1-pyridin-4-yl-propyl]-5-fluoro-1,3-dimethyl-1H-pyrazole-4-carboxamide (M+H=317).

PREPARATION EXAMPLE 3

Thionation of Amide of Formula (I) on Chemspeed Apparatus

In a 13 ml Chemspeed vial is weighted 0.27 mmol of phosphorous pentasulfide ($P_2S_5$). 3 ml of a 0.18 molar solution of the amide (I) (0.54 mmol) in dioxane is added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cartridge (2 g) and eluted twice by 8 ml of dichloromethane. The solvents are removed and the crude thioamide is analyzed by LCMS and NMR. Insufficiently pure compounds are further purified by preparative LCMS.

EXAMPLE A

In Vivo Test on *Sphaerotheca fuliginea* (Powdery Mildew)

The active ingredients tested are prepared by homogenization in a mixture of acetone/tween/DMSO/water. This suspension is then diluted with water to obtain the desired active material concentration.

Gherkin plants (Vert petit de Paris variety) in starter cups, sown on a 50/50 peat soil-pozzolana substrate and grown at 20° C./23° C., are treated at the cotyledon Z11 stage by spraying with the aqueous suspension described above. Plants, used as controls, are treated with an aqueous solution not containing the active material.

After 24 hours, the plants are contaminated by spraying them with an aqueous suspension of *Sphaerotheca fuliginea* spores (100,000 spores per ml). The spores are collected from contaminated plants. The contaminated gerkhin plants are incubated at about 20° C./25° C. and at 60/70% relative humidity.

Grading (% of efficacy) is carried out 21 days after the contamination, in comparison with the control plants.

Under these conditions, good (at least 70%) or total protection is observed at a dose of 500 ppm with the following compounds: 4, 5, 9, 10, 20, 21, 24, 27, 29, 31, 31, 32, 33, 34, 51, 77, 80, 81, 100, 102, 103 and 114.

EXAMPLE B

In Vivo Test on *Pyrenophora Teres* (Barley Net Blotch)

The active ingredients tested are prepared by homogenization in a mixture of acetone/tween/DMSO/water, then diluted with water to obtain the desired active material concentration.

Barley plants (Express variety), sown on a 50/50 peat soil-pozzolana substrate in starter cups and grown at 12° C., are treated at the 1-leaf stage (10 cm tall) by spraying with the active ingredient prepared as described above. Plants, used as controls, are treated with the mixture of acetone/tween/DMSO/water not containing the active material.

After 24 hours, the plants are contaminated by spraying them with an aqueous suspension of *Pyrenophora teres* spores (12,000 spores per ml). The spores are collected from a 12-day-old culture. The contaminated barley plants are incubated for 24 hours at about 20° C. and at 100% relative humidity, and then for 12 days at 80% relative humidity.

Grading is carried out 12 days after the contamination, in comparison with the control plants.

Under these conditions, good (at least 70%) or total protection is observed at a dose of 500 ppm with the following compounds: 4, 5, 9, 10, 11, 17, 18, 19, 20, 21, 24, 27, 28, 31, 32, 33, 81 and 103.

EXAMPLE C

In Vivo Test on *Mycosphaerella graminicola* (Wheat Leaf Spot)

The active ingredients tested are prepared by homogenization in a mixture of acetone/tween/DMSO/water, then diluted with water to obtain the desired active material concentration.

Wheat plants (Scipion variety), sown on a 50/50 peat soil-pozzolana substrate in starter cups, are treated at the 1-leaf stage (10 cm tall) by spraying with the aqueous suspension described above. Plants, used as controls, are treated with an aqueous solution not containing the active material.

After 24 hours, the plants are contaminated by spraying them with an aqueous suspension of *Mycosphaerella graminicola* spores (500,000 spores per ml). The spores are collected from a 7-day-old culture. The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 1, 4, 5, 9, 10, 11, 17, 18, 19, 20, 21, 24, 26, 28, 29, 31, 34, 35, 36, 42, 47, 48, 51, 52, 54, 61, 67, 74, 80, 81, 87, 96 and 102.

The invention claimed is:
1. A compound of formula (I)

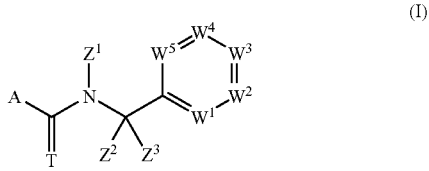

wherein
A represents a carbo-linked unsaturated or partially saturated, 5-membered heterocyclyl group that can be substituted by up to four groups $R^a$;

T is selected from the group consisting of O, S, $NR^c$, $N-OR^d$, $N-NR^cR^d$, and $N-CN$;

$Z^1$ represents a non substituted $C_3$-$C_7$-cycloalkyl or a $C_3$-$C_7$ cycloalkyl substituted by up to 10 atoms or groups independently selected from the group consisting of halogen atoms; cyano; $C_1$-$C_8$-alkyl; $C_1$-$C_8$-halogenoalkyl comprising up to 9 halogen atoms that can be the same or different; $C_1$-$C_8$-alkoxy; $C_1$-$C_8$-halogenoalkoxy comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; and di-($C_1$-$C_8$-alkyl)aminocarbonyl;

$Z^2$ and $Z^3$ are independently selected from the group consisting of a hydrogen atom; a halogen atom; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-alkynyl; cyano; nitro; $C_1$-$C_8$-alkoxy; $C_2$-$C_8$-alkenyloxy; $C_2$-$C_8$-alkynyloxy; $C_3$-$C_7$-cycloalkyl; $C_1$-$C_8$-alkylsulphenyl; amino; $C_1$-$C_8$-alkylamino; di-($C_1$-$C_8$-alkyl)amino; $C_1$-$C_8$-alkoxycarbonyl; $C_1$-$C_8$-alkylcarbonyl; $C_1$-$C_8$-alkylcarbamoyl; di-($C_1$-$C_8$-alkyl)carbamoyl; $N$-$C_1$-$C_8$-alkyl-$C_1$-$C_8$-alkoxycarbamoyl; or $Z^2$ and $Z^3$ together with the carbon atom to which they are linked can form a substituted or non substituted $C_3$-$C_7$ cycloalkyl;

$W^1$ to $W^5$ are independently represent selected from the group consisting of N and $CR^b$, at least one of $W^1$ to $W^5$ representing N and at least three of $W^1$ to $W^5$ representing $CR^b$;

each $R^a$ is independently selected from the group consisting of a hydrogen atom; halogen atom; cyano; nitro; amino; sulfanyl; hydroxyl; pentafluoro-λ-6-sulfanyl; $C_1$-$C_8$-alkylamino; di-($C_1$-$C_8$-alkyl)amino; tri($C_1$-$C_8$-alkyl)silyl; tri($C_1$-$C_8$-alkyl)silyl-$C_1$-$C_8$-alkyl; $C_1$-$C_8$-alkylsulfanyl; $C_1$-$C_8$-halogenoalkylsulfanyl comprising up to 9 halogen atoms that can be the same or different; $C_1$-$C_8$-alkyl; $C_1$-$C_8$-halogenoalkyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_1$-$C_8$-alkoxy; $C_1$-$C_8$-alkoxy-$C_1$-$C_8$-alkyl; $C_1$-$C_8$-halogenoalkoxy comprising up to 9 halogen atoms that can be the same or different; $C_2$-$C_8$-alkenyloxy; $C_2$-$C_8$-alkynyloxy; $C_3$-$C_7$-cycloalkyl; $C_3$-$C_7$-cycloalkyl-$C_1$-$C_8$-alkyl; $C_1$-$C_8$-alkylsulphinyl; $C_1$-$C_8$-alkylsulphonyl; $C_1$-$C_8$ alkoxyimino; ($C_1$-$C_8$-alkoxyimino)-$C_1$-$C_8$-alkyl; (benzyloxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; $C_1$-$C_8$-alkoxycarbonyl; $C_1$-$C_8$-halogenoalkoxycarbonyl comprising up to 9 halogen atoms that can be the same or different; and $C_1$-$C_8$-alkylaminocarbonyl; di-($C_1$-$C_8$-alkyl)aminocarbonyl;

each $R^b$ is independently selected from the group consisting of a hydrogen atom; halogen atom; nitro; cyano; hydroxyl; sulphanyl; amino; pentafluoro-λ6-sulphanyl; $C_1$-$C_8$-alkyl; $C_1$-$C_8$-halogenoalkyl comprising up to 9 halogen atoms that can be the same or different; $C_1$-$C_8$-alkylamino; di-($C_1$-$C_8$-alkyl)amino; $C_1$-$C_8$-alkoxy; $C_1$-$C_8$-halogenoalkoxy comprising up to 9 halogen atoms that can be the same or different; $C_1$-$C_8$-alkoxy-$C_1$-$C_8$-alkyl; $C_1$-$C_8$-alkylsulphanyl; $C_1$-$C_8$-halogenoalkylsulphanyl comprising up to 9 halogen atoms that can be the same or different; $C_1$-$C_8$-alkylsulphenyl, $C_1$-$C_8$-halogenoalkylsulphenyl comprising up to 9 halogen atoms that can be the same or different, $C_1$-$C_8$alkylsulphinyl, $C_1$-$C_8$-halogenoalkylsulphinyl comprising up to 9 halogen atoms that can be the same or different, $C_1$-$C_8$-alkylsulphonyl, $C_1$-$C_8$-halogenoalkylsulphonyl comprising up to 9 halogen atoms that can be the same or different; $C_2$-$C_8$-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different $C_2$-$C_8$-alkenyloxy; $C_2$-$C_8$-halogenoalkenyloxy comprising up to 9 halogen atoms that can be the same or different; $C_2$-$C_8$-alkinyloxy; $C_2$-$C_8$-halogenoalkinyloxy comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; formyloxy; formylamino; carboxy; carbamoyl; N-hydroxycarbamoyl; carbamate; (hydroxyimino)-$C_1$-$C_8$-alkyl; $C_1$-$C_8$-alkylcarbonyl; $C_1$-$C_8$-halogenoalkylcarbonyl comprising up to 9 halogen atoms that can be the same or different; $N$-$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl comprising up to 9 halogen atoms that can be the same or different; $C_1$-$C_8$-alkylaminocarbonyl; di-($C_1$-$C_8$-alkyl)aminocarbonyl; $C_1$-$C_8$-alkylcarbonyloxy; $C_1$-$C_8$-halogenoalkylcarbonyloxy comprising up to 9 halogen atoms that can be the same or different; $C_1$-$C_8$-alkylcarbonylamino; $C_1$-$C_8$-alkylaminocarbonyloxy; di-($C_1$-$C_8$-alkyl)aminocarbonyloxy; $C_1$-$C_8$-alkyloxycarbonyloxy; $C_1$-$C_8$-alkoxyimino; ($C_1$-$C_8$-alkoxyimino)-$C_1$-$C_8$-alkyl; ($C_1$-$C_8$-alkenyloxyimino)-$C_1$-$C_8$-alkyl; ($C_1$-$C_8$-alkynyloxyimino)-$C_1$-$C_8$-alkyl; (benzyloxyimino)-$C_1$-$C_8$-alkyl; tri($C_1$-$C_8$-alkyl)silyl; tri($C_1$-$C_8$-alkyl)silyl-$C_1$-$C_8$-alkyl; phenyl that can be substituted by up to 5 groups Q; benzyloxy that can be substituted by up to 5 groups Q; benzylsulphanyl that can be substituted by up to 5 groups Q; benzylamino that can be substituted by up to 5 groups Q; phenoxy that can be substituted by up to 5 groups Q; phenylamino that can be substituted by up to 5 groups Q; phenylsulphanyl that can be substituted by up to 5 groups Q; benzyl that can be substituted by up to 5 groups Q; pyridinyl that can be substituted by up to four groups Q and pyridinyloxy that can be substituted by up to four groups Q;

$R^c$ and $R^d$ are independently selected from the group consisting of a hydrogen atom; $C_1$-$C_8$-alkyl; $C_1$-$C_8$-halogenoalkyl comprising up to 9 halogen atoms that can be the same or different; $C_1$-$C_8$-alkoxy-$C_1$-$C_8$-alkyl; C2-C8-alkenyl; $C_2$-$C_8$-halogenoalkenyl comprising up to 9 halogen atoms that can be the same or different; $C_2$-$C_8$-alkynyl; $C_2$-$C_8$-halogenoalkynyl comprising up to 9 halogen atoms that can be the same or different; $C_3$-$C_7$-cycloalkyl; $C_3$-$C_7$-cycloalkyl-$C_1$-$C_8$-alkyl; $C_3$-$C_7$-halogenocycloalkyl comprising up to 9 halogen atoms that can be the same or different; formyl; $C_1$-$C_8$-alkylcarbonyl; $C_1$-$C_8$-halogenoalkylcarbonyl comprising up to 9 halogen atoms that can be the same or different; $C_1$-$C_8$-alkylsulphonyl; $C_1$-$C_8$-halogenoalkylsulphonyl comprising up to 9 halogen atoms that can be the same or different; phenyl that can be substituted by up to 5 groups Q; naphthyl that can be substituted by up to 6 groups Q; phenylmethylene that can be substituted by up to 5 groups Q; and phenylsulphonyl that can be substituted by up to 5 groups Q;

each Q is independently selected from the group consisting of a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms that can be the same or different; $C_1$-$C_8$-halogenoalkoxy comprising up to 9 halogen atoms that can be the same or different; tri($C_1$-$C_8$)alkylsilyl and tri($C_1$-$C_8$)alkylsilyl-$C_1$-$C_8$-alkyl; $C_1$-$C_8$-alkoxyimino; and ($C_1$-$C_8$-alkoxyimino)-$C_1$-$C_8$-alkyl;

as well as a salt, or an N-oxide, or a metallic complex, or a metalloidic complex, or an optically active isomer, or a geometric isomer thereof; provided that, when $W^2$ to $W^5$ are all $CR^b$, $R^b$ within $W^2$ to $W^5$ does not represent a $C_1$-$C_8$-alkyl or a $C_1$-$C_8$-halogenoalkyl when $W^1$ represents N and that, when $W^1$ to $W^4$ are all $CR^b$, $R^b$ within $W^1$ to $W^4$ does not represent a $C_1$-$C_8$-alkyl or a $C_1$-$C_8$-halogenoalkyl when $W^5$ represents N.

2. The compound of claim 1 wherein A is selected from the group consisting of:

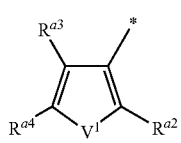
A¹

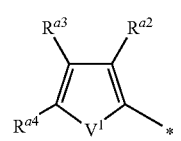
A²

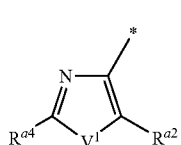
A³

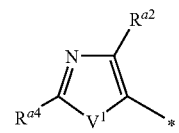
A⁴

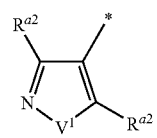
A⁵

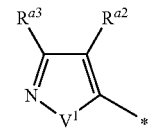
A⁶

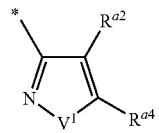
A⁷

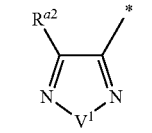
A⁸

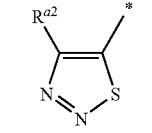
A⁹

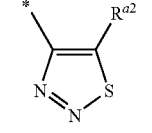
A¹⁰

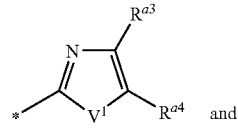
A¹¹ and

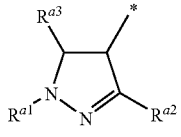
A¹² wherein:
- * represents the attachment point to the carbonyl group;
- $V^1$ represents O, S and $NR^{a1}$;
- $R^{a1}$ is selected from the group consisting of a hydrogen atom; $C_1$-$C_8$-alkyl; $C_1$-$C_8$-halogenoalkyl comprising up to 9 halogen atoms that can be the same or different; and $C_1$-$C_8$-alkoxy-$C_1$-$C_8$-alkyl;
- $R^{a2}$ and $R^{a3}$ are independently selected from the group consisting of a hydrogen atom; a halogen atom; cyano; $C_1$-$C_8$-alkyl; $C_1$-$C_8$-halogenoalkyl comprising up to 9 halogen atoms that can be the same or different; $C_1$-$C_8$- alkoxy or $C_1$-$C_8$-halogenoalkoxy comprising up to 9 halogen atoms that can be the same or different; and $C_3$-$C_7$-cycloalkyl;

$R^{a4}$ is selected from the group consisting of a hydrogen atom, a halogen atom; cyano; $C_1$-$C_8$-alkyl; $C_1$-$C_8$-halogenoalkyl comprising up to 9 halogen atoms that can be the same or different; $C_1$-$C_8$-alkoxy or $C_1$-$C_8$-halogenoalkoxy comprising up to 9 halogen atoms that can be the same or different; $C_3$-$C_7$-cycloalkyl; $C_1$-$C_8$-alkylsulfanyl; amino; $C_1$-$C_8$-alkylamino; di-($C_1$-$C_8$-alkyl)amino; and $C_1$-$C_8$-alkyloxycarbonyl.

3. The compound of claim 2 wherein A is selected from the group consisting of:

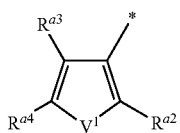
$A^1$

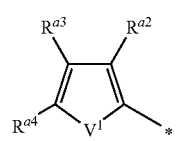
$A^2$

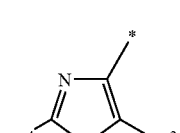
$A^3$

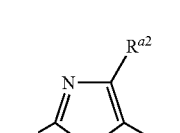
$A^4$

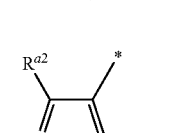
$A^5$

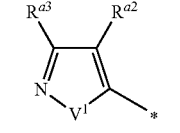
$A^6$

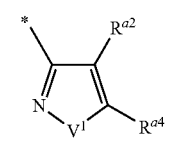
$A^7$

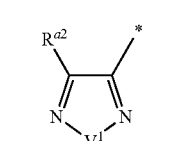
$A^8$

-continued

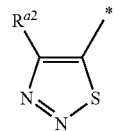
$A^9$

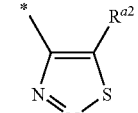
$A^{10}$

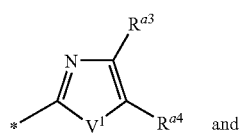
$A^{11}$ and

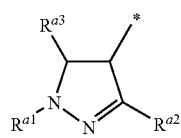
$A^{12}$ wherein:
-\* represents the attachment point to the carbonyl group;
$V^1$ is selected from the group consisting of O, S and $NR^{a1}$;
$R^{a1}$ is selected from the group consisting of a hydrogen atom; $C_1$-$C_8$-alkyl; and $C_1$-$C_8$-alkoxy-$C_1$-$C_8$-alkyl;
$R^{a2}$ is selected from the group consisting of $C_1$-$C_8$-alkyl; $C_1$-$C_8$-halogenoalkyl comprising up to 9 halogen atoms that can be the same or different; and $C_1$-$C_8$-alkoxy;
$R^{a3}$ represents is selected from the group consisting of a hydrogen atom; a halogen atom; $C_1$-$C_8$-alkyl; and
$R^{a4}$ is selected from the group consisting of a hydrogen atom, a halogen atom; $C_1$-$C_8$-alkyl; and $C_1$-$C_8$-halogenoalkyl comprising up to 9 halogen atoms that can be the same or different.

4. The compound of claim 2 wherein
A represents $A^5$;
$V^1$ represents $NR^{a1}$;
$R^{a1}$ represents $C_1$-$C_8$-alkyl;
$R^{a2}$ and $R^{a4}$ are independently selected from the group consisting of a hydrogen atom; a halogen atom; $C_1$-$C_8$-alkyl; and $C_1$-$C_8$-halogenoalkyl comprising up to 9 halogen atoms that can be the same or different.

5. The compound of claim 2 wherein
A represents $A^4$;
$V^1$ represents S;
$R^{a2}$ is selected from the group consisting of a $C_1$-$C_8$-alkyl; and $C_1$-$C_8$-halogenoalkyl comprising up to 9 halogen atoms that can be the same or different; and
$R^{a4}$ is selected from the group consisting of a hydrogen atom; $C_1$-$C_8$-alkyl; and $C_1$-$C_8$-halogenoalkyl comprising up to 9 halogen atoms that can be the same or different.

6. The compound of claim 1 wherein T is selected from the group consisting of an oxygen atom and a sulphur atom.

7. The compound of claim 1 wherein $Z^1$ represents cyclopropyl.

8. The compound of claim 1 wherein $Z^2$ and $Z^3$ are independently selected from the group consisting of a hydrogen atom and $C_1$-$C_8$ alkyl.

9. The compound of claim 1 wherein
W$^1$ represents N;
W$^2$ to W$^5$ independently represent CR$^b$; and
each R$^b$ is independently selected from the group consisting of a hydrogen atom; halogen atom; $C_1$-$C_8$-alkyl; $C_1$-$C_8$-alkoxy; $C_1$-$C_8$-halogenoalkoxy comprising up to 9 halogen atoms that can be the same or different; and phenoxy that can be substituted by up to 5 groups Q.

10. The compound of claim 1 wherein
W$^2$ represents N;
W$^1$ and W$^3$ to W$^5$ independently represent CR$^b$; and
each R$^b$ is independently selected from the group consisting of a hydrogen atom; halogen atom; $C_1$-$C_8$-alkyl; $C_1$-$C_8$-halogenoalkyl comprising up to 9 halogen atoms that can be the same or different $C_1$-$C_8$-alkoxy; $C_1$-$C_8$-halogenoalkoxy comprising up to 9 halogen atoms that can be the same or different; and phenoxy that can be substituted by up to 5 groups Q.

11. The compound of claim 1 wherein
W$^3$ represents N;
W$^1$, W$^2$, W$^4$ and W$^5$ independently represent CR$^b$; and
each R$^b$ is independently selected from the group consisting of a hydrogen atom; halogen atom; $C_1$-$C_8$-alkyl; $C_1$-$C_8$-halogenoalkyl comprising up to 9 halogen atoms that can be the same or different $C_1$-$C_8$-alkoxy; $C_1$-$C_8$-halogenoalkoxy comprising up to 9 halogen atoms that can be the same or different; and phenoxy that can be substituted by up to 5 groups Q.

12. The compound of claim 1 wherein Q is selected from the group consisting of a halogen atom; $C_1$-$C_8$-alkyl; $C_1$-$C_8$-alkoxy; $C_1$-$C_8$-halogenoalkyl comprising up to 9 halogen atoms that can be the same or different; and $C_1$-$C_8$-halogenoalkoxy comprising up to 9 halogen atoms that can be the same or different.

13. A fungicide composition comprising, as an active ingredient, an effective amount of a compound of formula (I) according to claim 1 and at least one agriculturally acceptable support, carrier or filler.

14. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

15. A method for controlling phytopathogenic fungi of crops, characterized in that an agronomically effective and substantially non-phytotoxic quantity of a composition according to claim 13 is applied to the soil where plants grow or are capable of growing, to the leaves and/or the fruit of plants or to the seeds of plants.

16. A compound of the formula:

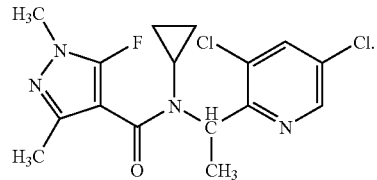

17. A fungicide composition comprising, as an active ingredient, an effective amount of a compound of the formula according to claim 16 and at least one agriculturally acceptable support, carrier or filler.

* * * * *